United States Patent
Signes Nuñez et al.

(10) Patent No.: US 8,399,228 B2
(45) Date of Patent: Mar. 19, 2013

(54) METHOD FOR RECOVERING ENERGY FROM THE ORGANIC FRACTION OF SOLID URBAN WASTE AND ASSOCIATED FACILITY

(75) Inventors: Vicente Signes Nuñez, La Alcudia (ES); Mercedes Ballesteros Perdices, Madrid (ES); Ignacio Ballesteros Perdices, Madrid (ES); Paloma Manzanares Secades, Madrid (ES); José Maria Martínez García, Madrid (ES); Maria José Negro Álvarez, Madrid (ES); José Miguel Oliva Domínguez, Madrid (ES); Rafael Castañeda Sánchez, Madrid (ES); Caterina Coll Lozano, Madrid (ES)

(73) Assignees: Industrias Mecanicas Alcudia, S.A., La Alcudia (Valencia) (ES); Centro de Investigaciones Energeticas Medioambientales y Tecnologicas (C.I.E.M.A.T.), Madrid (ES)

( * ) Notice: Subject to any disclaimer, the term of this patent is extended or adjusted under 35 U.S.C. 154(b) by 691 days.

(21) Appl. No.: 12/523,777

(22) PCT Filed: Feb. 14, 2008

(86) PCT No.: PCT/ES2008/000077
§ 371 (c)(1),
(2), (4) Date: Feb. 12, 2010

(87) PCT Pub. No.: WO2008/099038
PCT Pub. Date: Aug. 21, 2008

(65) Prior Publication Data
US 2010/0151550 A1 Jun. 17, 2010

(30) Foreign Application Priority Data
Feb. 15, 2007 (ES) .................................. 200700404

(51) Int. Cl.
*C12P 7/10* (2006.01)

(52) U.S. Cl. ........................................................ 435/165

(58) Field of Classification Search ............... 435/165
See application file for complete search history.

(56) References Cited

U.S. PATENT DOCUMENTS

| 4,094,740 | A | 6/1978 | Lang |
| 4,553,977 | A | 11/1985 | Fry |
| 4,874,134 | A | 10/1989 | Wiens |
| 4,894,066 | A | 1/1990 | Castelli |
| 5,407,817 | A | 4/1995 | Lightsey et al. |
| 5,503,996 | A | 4/1996 | Torget et al. |
| 5,932,456 | A | 8/1999 | Van Draanen et al. |

FOREIGN PATENT DOCUMENTS
WO 94/29474 12/1994

OTHER PUBLICATIONS

Aiduan Li & Majeda Khraisheh, "Municipal Solid Waste Used as Bioethanol Sources and its Related Environmental Impacts," International Journal of Soil, Sediment and Water, 2008, vol. 1, Issue 1, Article 5, pp. 1-7.
Aiduan Li, Blanca Antizar-Ladislao & Majeda Khraisheh, "Bioconversion of municipal solid waste to glucose for bio-ethanol production," Feb. 15, 2007.
International Search Report issued Aug. 1, 2008 in the International (PCT) Application of which the present application is the U.S. National Stage.
Hamelinck et al., "Ethanol from lignocellulosic biomass: techno-economic performance in short-, middle-, and long term," Biomass & Bioenergy, (2005), vol. 28, pp. 384-410.
L. R. Lynd, "Overview and evaluation of fuel ethanol from cellulosic biomass: technology, economics, the environment, and policy," Annu. Rev. Energy Environ., 1996, vol. 21, pp. 403-465.
C. E. Wyman, "Biomass Ethanol: Technical Progress, Opportunities, and Commercial Challenges." Rev. Energy Environ., 1999, vol. 24, pp. 189-226.
C. A. Cardona et al., "Energy consumption analysis of integrated flowsheets for production of fuel ethanol from lignocellulosic biomass," Energy 2006, vol. 31, pp. 2447-2459.

*Primary Examiner* — Maryam Monshipouri
(74) *Attorney, Agent, or Firm* — Wenderoth, Lind & Ponack, L.L.P.

(57) ABSTRACT

The invention relates to a method for recovering energy from the organic fraction of urban solid waste comprising the following steps: a) the organic fraction is pre treated with mineral acids, preferably sulfuric acid, during which the fraction is heated by an outer thermal jacket with no steam injection or steam explosion, thereby producing a first slurry containing an insoluble solid susceptible to enzymatic attack by cellulases; b) a step comprising enzymatic hydrolysis using cellulases and simultaneous fermentation, using an ethanologenic microorganism, of the first slurry in order to obtain a second slurry containing diluted ethanol; and c) distillation of the second slurry such as to obtain wet ethanol, a recyclable liquid effluent and a solid.

9 Claims, 18 Drawing Sheets

METHOD FOR RECOVERING ENERGY FROM THE ORGANIC FRACTION OF SOLID URBAN WASTE AND ASSOCIATED FACILITY

This application is a 371 of PCT/ES2008/000077 filed Feb. 14, 2008, which claims foreign priority to Spanish application P200700404 filed Feb. 15, 2007.

FIELD OF THE INVENTION

The present invention belongs to the field of energy production from Urban Solid Waste (U.S.W.).

The general aim concerns a procedure for the recovery of energy from the organic fraction of Urban Solid Waste (U.S.W.). An additional object concerns the obtention of ethanol in an efficient way and at a cost that makes it possible the industrial application of this technology.

BACKGROUND OF THE INVENTION

The fact that a significant fraction of Urban Solid Waste (U.S.W.) (paper, vegetables, food and wood) contributes in an important way to the Urban Solid Waste content of cellulose, potentially convertible into glucose by hydrolysis and then into ethanol by fermentation, has encouraged some countries to develop this route in order to create a new source of renewable energy (bioethanol), at the same time as reducing the growth of U.S.W. The use of the organic fraction of U.S.W. as raw material for the production of ethanol would allow the recovery of waste by the obtention of clean fuel with a great future.

A first solution for the ever greater accumulation of U.S.W. has been the utilization of that fraction with acceptable characteristics as fuel, in such a way that thermal and electrical energy are simultaneously produced (cogeneration), or exclusively electrical energy (generation) is produced. In this type of activities, profitability is not the sole factor to take into account.

The use of U.S.W. as raw material for the production of ethanol fuel can help not just to release the pressure caused by an increase in the surface of the dump, but also to provide energy in the most sustainable way possible. The facilities for transforming U.S.W. into ethanol would be able to provide a local solution to the accumulation of this waste, without requiring any thermal process (which generates great social opposition), and using instead of thermal processes a widely accepted biotechnological process of hydrolysis and fermentation. The organic fraction of U.S.W. does not have the problem of collection and transport raised by agricultural waste since it is systematically collected in well-established treatment plants. Moreover, these raw materials for ethanol production are not subject to seasonality, so that their availability and storage raise fewer problems than agricultural waste.

Raw materials for the production of renewable biofuels currently have their prices tied to markets that are not directly related to the automotive fuel market. The cost of sugar and cereals is regulated by food markets and their prices are high. The search for low-cost raw materials as alternatives to traditional ones is crucial for reducing costs in the production of bioethanol and for ensuring the profitability of projects. The use of lignocellulose biomass is, in the medium term, the most promising option for obtaining ethanol fuel at low cost.

The production of ethanol starting from U.S.W. would provide a revolutionary solution to various environmental problems since it generates a renewable fuel at the same time as eliminating waste.

There exist developments of some technologies for processing of cellulose found in U.S.W., though there are no industrial facilities in operation. In the last decade, intensive research has been conducted in this area, primarily in the United States, and various alternatives have been considered based on acid hydrolysis (Masada Resource in the USA) and enzymatic hydrolysis (Iogen in Canada). In Europe there do not exist any developments that could provide technologies that will produce a solution for all the stages that are required in a complete U.S.W. transformation process.

The production of ethanol starting from matter of agricultural origin has been a sufficiently developed technology at the industrial level since the end of World War Two. Nevertheless, these technologies have not been applied for treatment of U.S.W., specifically its cellulose fraction, no doubt due to the greater complexity entailed and the lower yields in ethanol production that are achieved.

Various patents have so far protected different variants of methods for the treatment of waste and the obtention of biofuels, among others:

U.S. Pat. No. 4,009,075 discloses a method for manufacturing alcohol—ethanol—starting from cellulose material coming from waste, by means of hydrolyzing that material into sugars and subjecting the resulting mixture to simultaneous digestion and fermentation in order to convert the sugar into alcohol and using an inoculum containing a cellulose enzyme and yeast. The method comprises the sterilization of the cellulose material, distillation in vacuo in order to isolate the alcohol and the recovery of the inoculum for its reuse. The sterilization of the cellulose material consists of a treatment with steam, sufficient for eliminating strains of bacteria that can cause undesired reactions.

ES-2166316 discloses a method for the production of ethanol starting from lignocellulose biomass, which comprises carrying out a pretreatment of the biomass consisting of grinding the biomass and subjecting it to steam explosion at a temperature of 190-230° C. for between 1 and 10 minutes, collecting the pretreated material in a cyclone, separating the liquid and solid fractions by means of filtration, treating the solid material in a fermenter, adding a cellulase and β-glucosidase and inoculating the fermenter with *Kluveromyces marxianus*.

U.S. Pat. No. 3,990,944 discloses a method for obtaining ethanol by means of reactions under anaerobic conditions of a cellulose material, a cellulase and a microorganism that produces alcohol, the starting materials coming from agricultural crops such as rice straw, wheat straw, wood, cotton, corn leaves, even newspapers, corrugated board and bits of paper. The starting material is broken up and sterilized using heat and, simultaneously to the enzymatic hydrolysis by means of the addition of cellulase—or a producer microorganism of cellulase—the microorganism is added (for example, *Saccharomyces cerevisiae*) that produces the fermentation to alcohol.

U.S. Pat. No. 6,267,309 discloses a method for producing ethanol starting from urban solid waste which—according to one embodiment—comprises a pretreatment with dilute sulfuric acid in order to solubilize the remaining heavy metals and produce a soluble component and another insoluble one, separate the soluble component from the insoluble one, dry the insoluble component, treat the insoluble component with concentrated sulfuric acid in order to provide a partially hydrolyzed mixture, dilute said mixture, stir and separate the solids, concentrate the filtrate in order to obtain a part rich in sugar and to ferment the sugar. No simultaneous enzymatic hydrolysis and fermentation is carried out.

U.S. Pat. No. 5,407,817 discloses a method for treating solid waste that comprises its pretreatment with dilute sulfuric acid in order to reduce the heavy metal content, this method being similar to that disclosed by U.S. Pat. No. 6,267,309.

U.S. Pat. No. 4,321,328 discloses a method for producing ethanol starting from materials containing cellulose, which comprises saccharification, fermentation and distillation in order to recover ethanol, though in which the saccharification and fermentation are carried out separately.

EP-0005703 discloses a method for treating waste such as wastewater, domestic waste, etc., according to which the waste—after eliminating recyclable materials such as glass, etc.—is hydrolyzed by sulfurous anhydride—present in the water—in order to convert the hydrolyzable compounds into fermentable materials and finally into fuel such as ethanol. The saccharification and fermentation are carried out separately.

GB-1,604,948 discloses a method for simultaneously obtaining liquid fuel and a nutritive product starting from solid waste. Said method comprises subjecting the biomass to acid hydrolysis and converting it into a fermentable sugar. The acid hydrolysis is produced in the presence of sulfurous acid. No enzymatic hydrolysis is carried out.

U.S. Pat. No. 4,093,516 discloses a method for converting urban waste into liquid fuel, said method comprising partial concentration, saccharification, fermentation and distillation. The hydrolysis and saccharification are carried out simultaneously using chemicals and then—after deactivating the hydrolytic component and adjusting the pH and solid contents—the fermentation is carried out. No enzymatic hydrolysis is carried out simultaneously with the fermentation.

U.S. Pat. No. 4,237,226 discloses a method for treating cellulose substances prior to their hydrolysis with the aim of increasing the sugar yield and reducing the time for that hydrolysis. The hydrolysis can be chemical or enzymatic. This patent is therefore directed to a pretreatment of the cellulose material and does not disclose any later stage of fermentation and recovery of alcohol.

WO-9012103 discloses a method for producing alcohol starting from waste containing cellulose, and which comprises separating the materials that do not contain cellulose, hydrolyzing the cellulose materials using chemicals or enzymes, adjusting the pH in a storage tank, fermenting in a fermenter, eliminating solids and distilling the ethanol.

EP-1,690,944 discloses a method for obtaining alcohol starting from lignocellulose materials, which comprises chemical and/or physical pretreatment of a cellulose or lignocellulose substrate, enzymatic hydrolysis of the pretreated substrate and ethanolic fermentation by a microorganism.

Among the unpatented literature related to the present invention, the following publications can be cited:

Ballesteros, I., Oliva, J. M., Negro, M. J., Manzanares, P., Ballesteros, M. *Applied Biochemistry and Biotechnology*, 98-100, 717-732 (2002);

Ballesteros, I., Oliva, J. M., Negro, M. J., Manzanares, P., Ballesteros, M. *Process Biochemistry*, 38(2), 187-192 (2002);

Ballesteros, I., Oliva, J. M., Negro, M. J., Manzanares, P., Ballesteros, M. *Grasas y Aceites*, 53(3), 282-288 (2002);

Ballesteros, M., Oliva, J. M., Manzanares, P., Negro, M. J., Ballesteros, I. *World Journal of Microbiology & Biotechnology*, 8, 559-561 (2002);

Negro, M. J., Manzanares, P., Ballesteros, I., Oliva, J. M., Cabañas, A., Ballesteros, M. *Applied Biochemistry and Biotechnology*, 105-108, 87-100 (2003);

Oliva, J. M., Saez, F., Ballesteros, I., González, A., Negro, M. J., Manzanares, P., Ballesteros, M. *Applied Biochemistry and Biotechnology*, 105-108, 141-153 (2003);

Negro, M. J., Manzanares, P., Oliva, J. M., Ballesteros, I., Ballesteros, M. *Biomass and Bioenergy*, 25, 301-308 (2003);

Oliva, J. M., Ballesteros, I., Negro, M. J., Manzanares, P., Ballesteros, M. *Process Biochemistry*, 39, 1843-1848 (2004);

Oliva, J. M., Ballesteros, I., Negro, M. J., Manzanares, P., Ballesteros, M. *Biotechnology Progress* 20 (3), 715-720 (2004);

Oliva, J. M., Manzanares, P., Ballesteros, I., Negro, M. J., González, A., Ballesteros, M. *Applied Biochemistry and Biotechnology*, 121-124, 887-99 (2005).

The application of the new method for the treatment of urban waste will permit the recovery of a waste, reducing the harmful effects caused by the accumulation of urban solid waste in controlled dumps.

SUMMARY OF THE INVENTION

The invention relates to a method for recovering energy from the organic fraction of urban solid waste comprising the following steps:
   a) Pretreatment of said organic fraction with mineral acids—preferably sulfuric acid—by means of heating by an outer thermal jacket with no steam injection or steam explosion, producing a first slurry containing an insoluble solid susceptible to enzymatic attack by cellulases;
   b) a step comprising enzymatic hydrolysis by cellulases and simultaneous fermentation, using an ethanologenic microorganism, of the first slurry, in order to obtain a second slurry containing diluted ethanol;
   c) distillation of said second slurry such as to obtain wet ethanol, a recyclable liquid effluent and a solid.

In the method for treating the waste fraction, the fraction of sugars of the urban solid waste, which can be composted or not, is used in particular and is preferably in the form of compost.

Recyclable materials are previously removed from the urban solid waste so that it can be used in the method of the invention.

Moreover, removing part of the inorganic components (silica) contained in the waste increases the organic matter content of the waste.

The feed of raw material can be done by means of mechanical devices, which prevent the entrance of soils and metals, usually present in urban solid waste, into the pretreatment zone.

The method starts by subjecting the U.S.W. to a process of acid hydrolysis diluted at low pressure and moderate temperature under the conditions previously stated for the pretreatment stage. The lignocellulose material from that solid waste is chemically attacked in such a way that, on the one hand, the lignocellulose structure is debilitated and, on the other, the hemicellulose fraction is hydrolyzed obtaining mainly xylose. In this process, the xylose is not used for its fermentation to bioethanol.

The weakening of the lignocellulose structure allows opening channels with access to the core of the lignocellulose material where the cellulose is located. In this way, the cellulose will be able to be hydrolyzed to glucose and then fermented to ethanol by the action of enzymes and yeasts, respectively.

The pretreatment stage with acid is carried out at an acid concentration of between 0.1% and 5% by volume, preferably at a concentration of between 0.2% and 1.5% by volume, more preferably between 0.5% and 1% by volume.

According to the method of the invention, the pretreatment stage with acid is preferably carried out at a temperature of between 100 and 180° C., more preferably between 120 and 140° C.

According to the inventive method, the pretreatment stage with acid is preferably carried out with a residence time of between 30 and 90 minutes, more preferably between 40 and 60 minutes.

The pretreatment stage with acid is carried out with a initial charge of solids (substrate) of between 5 and 40% weight/volume, preferably between 10 and 30% weight/volume.

In a preferred embodiment, the pretreatment stage with acid is carried out with sulfuric acid at a concentration of between 0.5% and 1% by volume, at a temperature of between 120 and 140° C., with a residence time of between 40 and 60 minutes, and with a charge of solids of between 10 and 30% weight/volume.

The pretreatment stage with acid is preferably carried out in a reactor, complete mixing type, of conical design and with internal stirring by means of an Archimedes screw.

A specially preferred embodiment comprises preparing in the pretreatment stage a 30% by weight suspension of composted organic fraction and subjecting it to an acid hydrolysis with sulfuric acid diluted at 1% v/v of acid in water, at 121° C. and 1 bar, this stage being carried out in 1 hour in a perfectly mixed type reactor, of conical design and with internal stirring by means of an Archimedes screw.

In the method of the invention, genetically modified microorganisms can be used for acting on sugars that are currently "non"-fermentable (xylose, arabinose, etc.).

Next, i.e., following the pretreatment stage, partial neutralization of the first slurry is carried out prior to subjecting it to the enzymatic hydrolysis stage by celluloses and fermentation. The aim of said partial neutralization is to achieve a slightly acid pH suitable for the following stage.

According to a particular embodiment in the pretreatment stage the temperature of the pretreated media is preferably lowered to approximately 42° C. and is neutralized with dilute caustic soda until a pH of between 4.8 and 5.5 is achieved, using a neutralizing agent and subjecting it to gentle stirring in order to facilitate the neutralization.

The first prehydrolyzed slurry coming from the previous stage is subjected to a period of simultaneous saccharification and fermentation for several days. In the saccharification stage, the cellulose is hydrolyzed to glucose by the action of cellulases. In the fermentation stage, the glucose is transformed to ethanol by the action of yeast. Both stages occur simultaneously. During this stage, the heat of fermentation that is generated is eliminated by means of an appropriate cooling system by recirculation of the actual fermentation broth.

According to a particularly preferred embodiment, in the stage of simultaneous hydrolysis and fermentation, an ethanol yeast producer is used at a temperature between 35° C. and 42° C., using cellulases at an amount of between 10 and 40 FPU/gram of cellulose and times no greater than 140 hours.

The yeast can, for example, be *K. marxianus*.

Nutrients can be used during the fermentation which act as accelerators and reduce the time that the same requires.

The second slurry, obtained in the fermentation stage, is distilled in the conventional way in the distillation unit. The distillation of the second slurry is carried out in two stages: rectification by means of steam stripping, and azeotropic distillation.

In the rectification stage, a wet ethanol is obtained that is sent to azeotropic distillation along with an aqueous suspension that is sent to effluents treatment, where the solid is obtained. In azeotropic distillation, azeotropic ethanol is obtained, which is also wet and is dried in a sieve such as a zeolite, along with a liquid effluent which is returned to the first distillation or rectification stage.

In the rectification stage the bioethanol is separated from the heavy fraction of the aqueous suspension coming from the outlet of the fermenters. The ethanol thus obtained has a considerable water content that requires an additional distillation stage for reducing it to the content corresponding to the ethanol-water azeotrope. The two main streams of this stage of the method are the bioethanol of azeotropic composition and a liquid effluent which is returned to the first distillation stage.

The azeotropic ethanol is stored until it is sent to the tanks, moment at which it is dried by means of a molecular sieve. This operation takes place in the facility dehydration unit.

The aqueous fraction coming from the distillation unit is subjected to an evaporation process in order to eliminate the solid fraction (the solid of stage c) of the distillation) and recover most of the water, which will be subjected to a biological treatment process, secondary level in principle, in order to eliminate as much as possible the soluble organic components which, in theory, are of no interest and could prevent the correct displacement of the saccharification and fermentation reactions.

The second slurry obtained following the SFS stage is subjected to solids-ethanol-water separation by means of a stripping process in the rectification column of the distillation stage.

The rectification column preferably consists of screen plates in order to achieve the double objective of the ethanol separation, by steam stripping, and a third slurry.

According to an additional particular embodiment, the distillation stage is optimized until it is obtained a final product purity that will allow its commercialization in the market.

The liquid fraction obtained in the first stage of distillation, i.e., in the rectification stage, is subjected to a vacuum flash evaporation that will allow the recovery of approximately 90% of the water used in this process.

The solid waste obtained in the flash evaporation stage can be used as solid fuel for a cogeneration boiler for the production of thermal and electrical energy by means of turbines.

An additional object of the present invention is the use of the method for producing ethanol using the organic fraction of urban solid waste as raw material, preferably in the form of composted waste.

An additional object of the present invention is to develop a viable alternative, from the environmental point of view, to the treatment of urban solid waste, minimizing the negative effects of its accumulation in controlled dumps.

Another object is also the use of the solid waste generated after the ethanol production process for its energy recovery by a heat and/or electricity production process through combustion.

Besides, the present invention is also related to a facility for the treatment of organic fraction of urban solid waste by a method comprising the following steps:
 a) Pretreatment of said organic fraction with mineral acids—preferably sulfuric acid—by means of heating by an outer thermal jacket with no steam injection or steam explosion, producing a first slurry containing an insoluble solid susceptible to enzymatic attack by cellulases;

b) a step comprising enzymatic hydrolysis by cellulases and simultaneous fermentation, using an ethanologenic microorganism of said first slurry in order to obtain a second slurry containing diluted ethanol;

c) distillation of said second slurry to obtain wet ethanol, a recyclable liquid effluent and a solid.

Said facility for the treatment of urban solid waste comprises at least:

a pretreatment unit (100) of the organic fraction of the waste, which comprises at least one charging section and at least one prehydrolysis section;

a simultaneous hydrolysis and fermentation unit (300); and a distillation unit (400) that comprises at least one rectification section and at least one azeotropic distillation section.

Optionally, it also comprises a unit for the treatment of effluents (600), as well as a unit for the preparation and handling of the waste.

The facility of the present invention can moreover include an ethanol dehydration unit.

The facility of the present invention can furthermore comprise:

at least one steam generation unit;
at least one water cooling unit;
at least one cold water unit;
at least one unit of plant air and instruments; and
fuel storage means.

The facility can also comprise a laboratory for the control of the facility.

According to particular embodiments, the pretreatment unit comprises at least:

a vessel for the preparation of the reactors feed (V-101);
a feed pump to reactors (P-101);
a vessel for the reactor product (V-102);
a feed pump to fermenters (P-102);
prehydrolysis reactors (R101);
a cooling pump for the reactors;
a prehydrolysis cooler (E-101).

The first stage of the method takes place in the pretreatment unit. In this unit, the U.S.W. is subjected to a process of dilute acid hydrolysis with mineral acids, preferably sulfuric acid, under the conditions described earlier for the method of the invention.

According to the invention, the raw material can be urban solid waste following the recovery of the recyclable materials, either composted or without composting. The content in sugars is around 25% (of dry weight) of the raw material.

According to particular embodiments, the simultaneous hydrolysis and fermentation unit comprises at least:

a fermenter vessel (V-301/304);
a fermentation product pump (P-301/304); and
a coolant for the fermentation broth (E-301/304).

According to particular embodiments, the distillation unit comprises at least:

a feed vessel (V-401);
a feed pump (P-401);
a rectifying column (T-401);
a first column condenser (E-402);
a first column boiler (E-401);
a safety valve vessel (V-402);
an azeotropic column (T-402);
a second column condenser (E-404);
a second column boiler (E-403);
a bioethanol cooler (E-405); and
a bottom pump (P-402).

The dehydration unit for the ethanol can comprise at least:

a wet bioethanol tank (V-501);
a wet bioethanol pump (P-501);
a bioethanol cooler (E-501); and
a drying tower (T-501).

The unit for the treatment of effluents (600) can comprise at least:

a vacuum evaporation section, which comprises at least:
    a vacuum separator (V-601);
    a concentrates pump (P-601); and
    an evaporator (E-601); and
a recovered water condensation section, which comprises at least:
    a recovered water accumulator (V-602);
    a pump for water to treatment (P-602);
    an ejector (K-601);
    a pre-condenser (E-602); and
    a post-condenser (E-603).

Preferably, the facility of the present invention comprises:

a pretreatment unit for the organic fraction of the waste, which comprises a charging section and a prehydrolysis section;
a simultaneous hydrolysis and fermentation unit;
a distillation unit comprising a rectification section and an azeotropic distillation section;
a dehydration unit for the ethanol;
a unit for the treatment of effluents, which comprises:
    a vacuum evaporation section and
    a recovered water condensation section
a unit for the preparation and handling of the waste;
a steam generation unit;
a cooling water unit;
a cold water unit;
a unit of plant air and instruments; and
fuel storage means.

DETAILED DESCRIPTION OF A PREFERRED EMBODIMENT OF THE INVENTION

A preferred embodiment of the facility of the invention is shown in FIGS. 1 to 17. According to this embodiment, the raw material is stored in at least one charge hopper with a truncated-pyramidal shape and at least one rotary valve. From this charge hopper, the raw material is transported via a drain pipe with a vibrator motor for the elimination of the earth or sand rests present in the raw material. The charge hopper is then fed by means of a bucket elevator. From the charge hopper the raw material is carried to a crusher where the particle size is reduced to 1-2 mm. A magnetic separator is then fed by means of a worm screw in order to retain any possible particles of iron present in the waste. From the crusher, the grinded material is unloaded to the reception hopper by means of a pneumatic system. From the reception hopper the amount of raw material is dosed to the pretreatment reactors by means of a weighing cell, shown in FIG. 1. The amount of water needed to achieve a solid/liquid ratio of 1/10 is added to the reception hopper, where it is kept under stirring for between 30 and 60 minutes in order to ensure the absence of inorganic solids.

From the reception hopper the pretreatment reactors are fed (FIGS. 2A and 2B) by means of a feed pump. The pretreatment reactors are conical-vertical design reactors with Archimedes type screw stirrers and, once the suspension of raw material and water is introduced into the pretreatment reactor, the appropriate amount of acid is added, it is stirred and the temperature is raised to the appropriate conditions (FIGS. 1, 2A and 2B). The pretreatment unit consists according to this embodiment of at least: a charging and prehydrolysis section (FIG. 1) which comprises: a vessel for the preparation of the charge to the reactors (V-101); a feed pump to reactors, a vessel for the reactor product (V-102), a feed pump to fermenters (P-102), an input (E) for organic waste, prehydrolysis reactors (R101) which are shown in FIGS. 2A and 2B, a reactors cooling pump and a prehydrolysis cooler (E-101) shown in FIG. 3.

According to this preferred embodiment, in the simultaneous hydrolysis (saccharification) and fermentation unit (FIG. 4), the prehydrolyzed product coming from the previous stage is subjected to a simultaneous hydrolysis (saccharification) and fermentation, as described previously. The heat of fermentation that is generated is eliminated by means of a suitable cooling system by recirculation of the fermentation broth. This unit comprises at least: a fermenter vessel (V-301/304), a fermentation product pump (P-301/304), and a coolant for the fermentation broth (E-301/304).

Once fermented, the product is distilled in a conventional way in the distillation unit (FIGS. 6 and 7) which basically consists of two sections, each of them relating to a stage of the same name: rectification (FIG. 6) and azeotropic distillation (FIG. 7) as has been described earlier. The distillation unit comprises at least: a rectifying column (T-401), a first column condenser (E-402), a first column boiler (E-401) and a safety valve vessel (V-402), shown in FIG. 6, a feed vessel (V-401), a feed pump (P-401), an analyzer (A-401) shown in FIG. 5, and an azeotropic column (T-402), a second column condenser (E-404), a second column boiler (E-403), a bioethanol cooler (E-405) and a bottom pump (P-402), shown in FIG. 7.

According to this same embodiment, the azeotropic ethanol is dried by means of a molecular sieve. This operation takes place in the dehydration unit (500) (FIG. 8), which comprises at least a wet bioethanol tank (V-501), a wet bioethanol pump (P-501), a bioethanol cooler (E-501) and a drying tower (T-501).

According to this same embodiment, the aqueous fraction, coming from the distillation unit, is subjected to an evaporation process in order to eliminate the solid fraction and recover most of the water, which will be subjected to a process of biological treatment. All these operations take place in the effluent treatment unit, which is shown in FIG. 9, and which comprises at least: a vacuum evaporation section, which in turn comprises at least a vacuum separator (V-601), a concentrates pump (P-601) and an evaporator (E-601), shown in FIG. 9; and at least a recovered water condensation section, which in turn comprises at least: a recovered water accumulator (V-602), a pump for the water to treatment (P-602), an ejector (K-601), a pre-condenser (E-602) and a post-condenser (E-603).

According to this embodiment, the facility furthermore comprises a unit for the preparation and handling of the waste, a steam generation unit, a cooling water unit, a cold water unit, a unit of plant air and instruments and fuel storage means.

In accordance with this embodiment, the facility can also include other units for storage and dosing of chemicals and the appropriate auxiliary services for achieving its operation.

By means of the method of the present invention, the protection and regeneration of the soil will be achieved, being able to close uncontrolled points for dumping urban waste and to recover these degraded spaces.

The facility for carrying out the method of the invention can transform 500 t/day of U.S.W.

The present invention provides the following advantages:

There is no need to carry out any pretreatment of the lignocellulose biomass by steam explosion.

The obtention of a product with a high energy demand on the automotive market: dehydrated ethanol.

The conversion of U.S.W. into an inert solid byproduct of suitable characteristics for its use as fuel in the process itself.

The self-generation of the electrical and thermal energy required by the process by means of some cogeneration system (simple cycle with steam turbine, simple cycle with gas turbine or combined cycle).

The exporting and sale of electricity generated in excess by the cogeneration system that is introduced.

With the facility of the present invention, at least 2 to 5 tons of waste a day will be able to be processed.

LIST OF REFERENCES USED IN THE FIGURES

Figure 1:
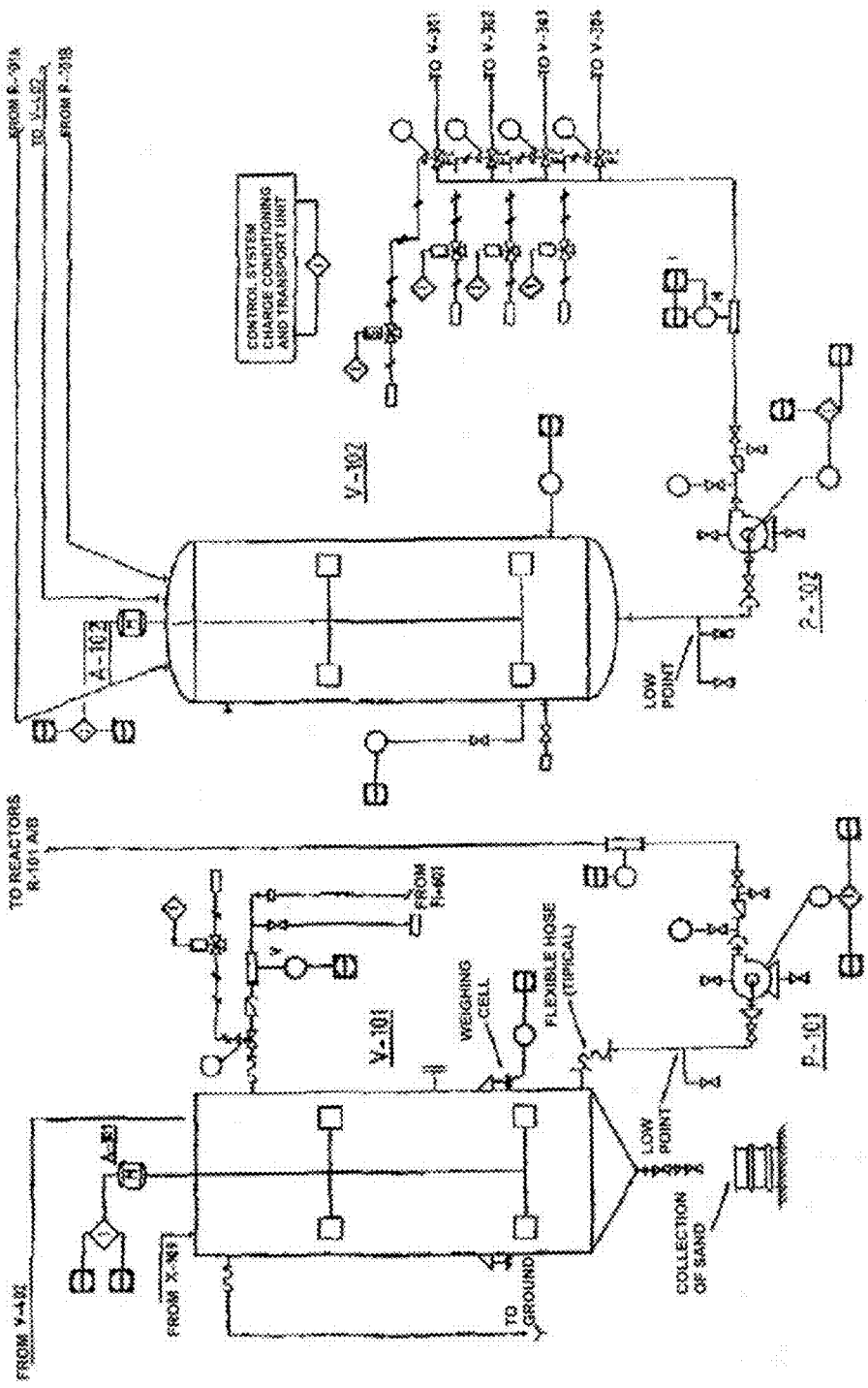
FIG. 1 shows the charging and prehydrolysis section of the pretreatment unit (100).
Figure 2A:
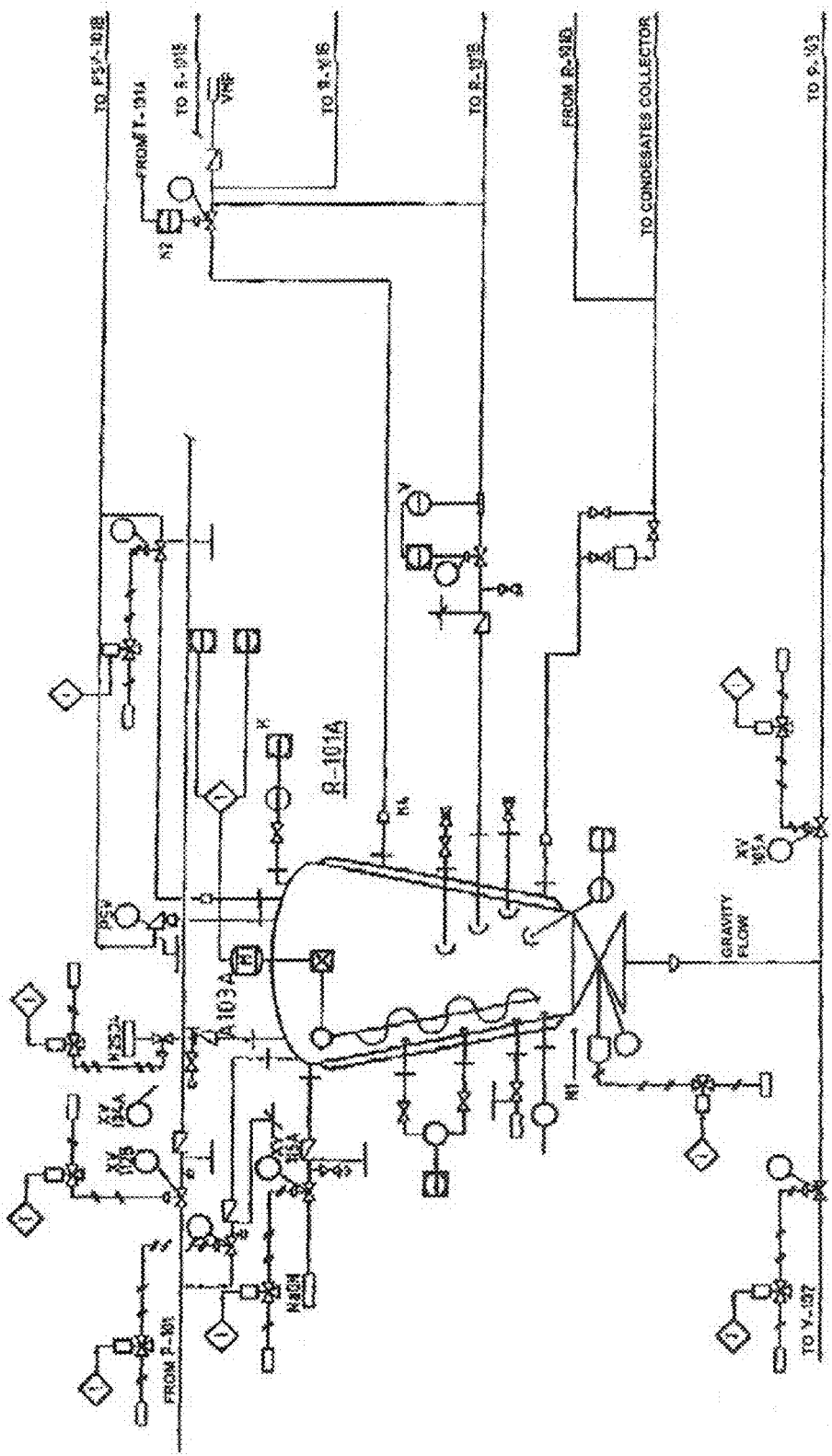
FIGS. 2A and 2B show the prehydrolysis section of the pretreatment unit (100).
Figure 2B:
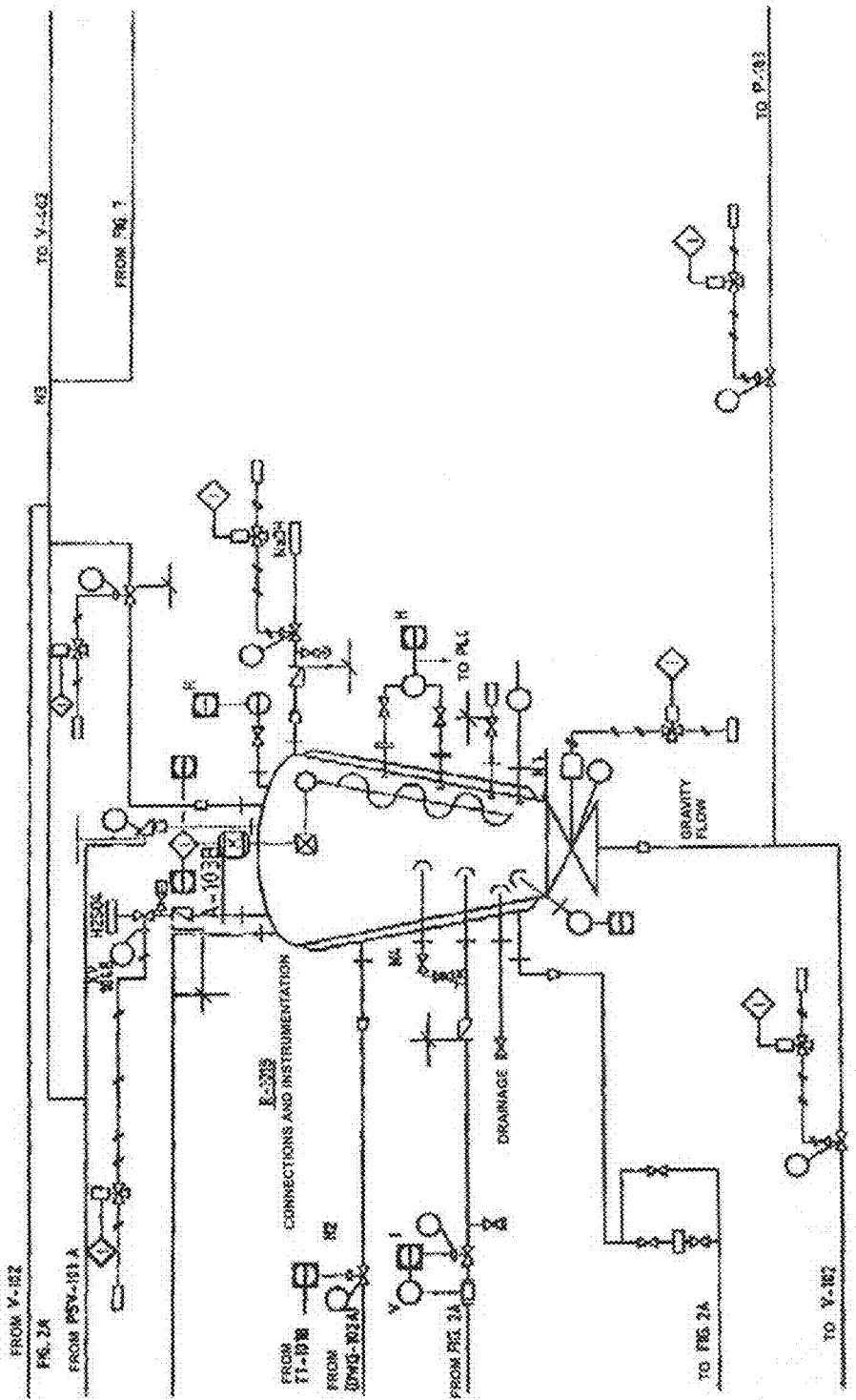
Figure 3:
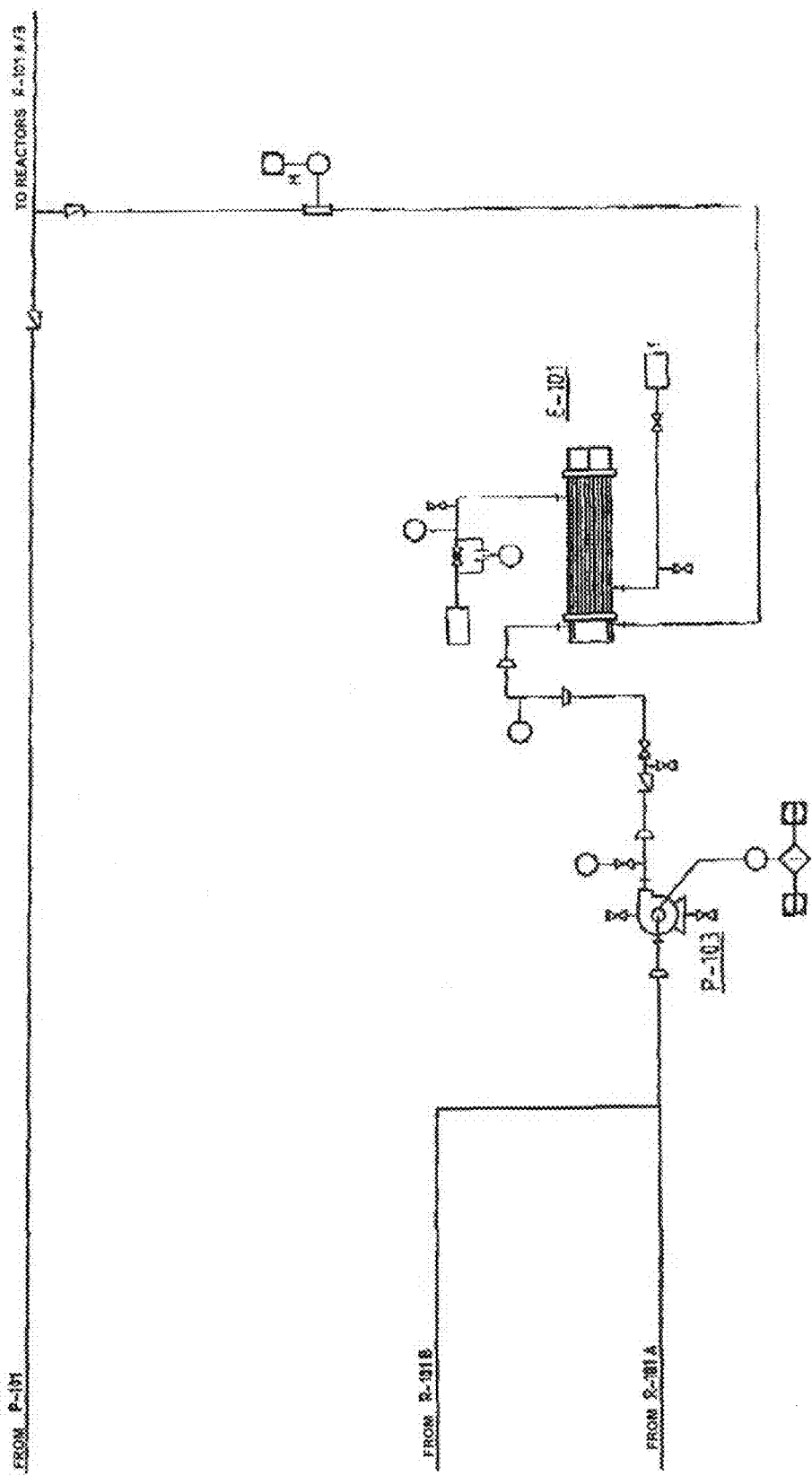
FIG. 3 shows the cooling and prehydrolysis section of the pretreatment unit (100).
Figure 4:
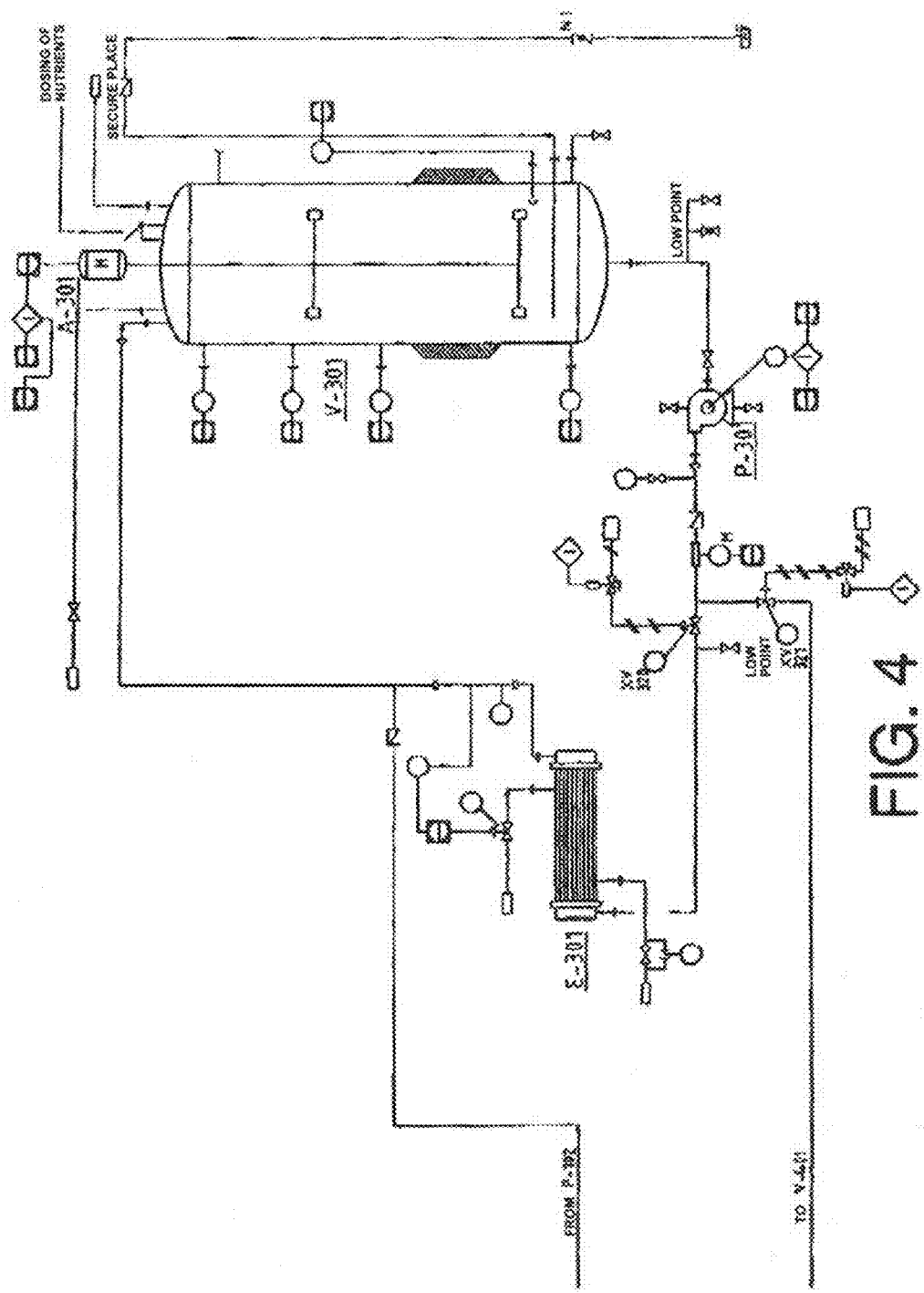
FIG. 4 shows the fermentation unit (300).
Figure 5:
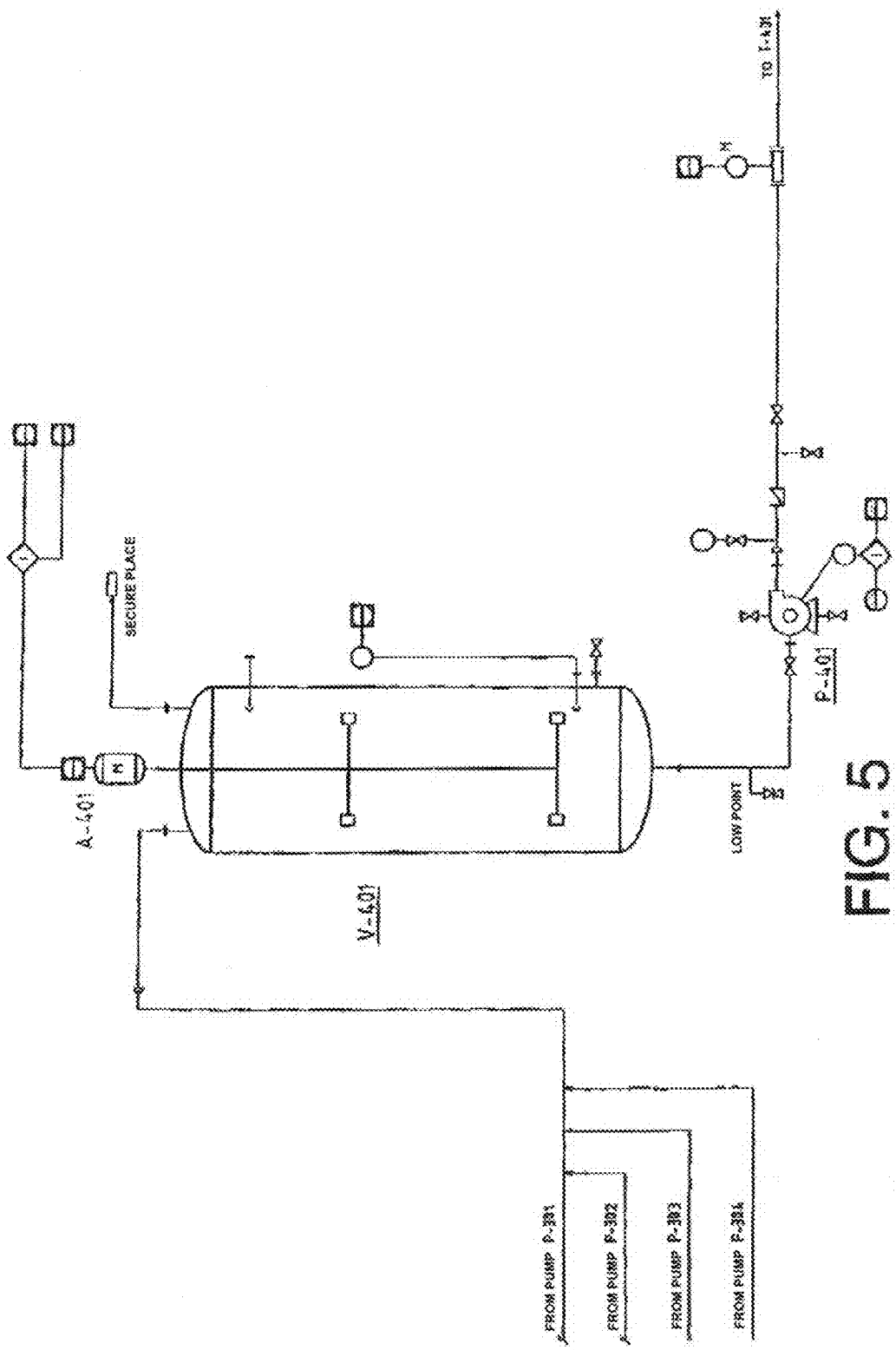
FIG. 5 shows the distillation unit (400).
Figure 6:
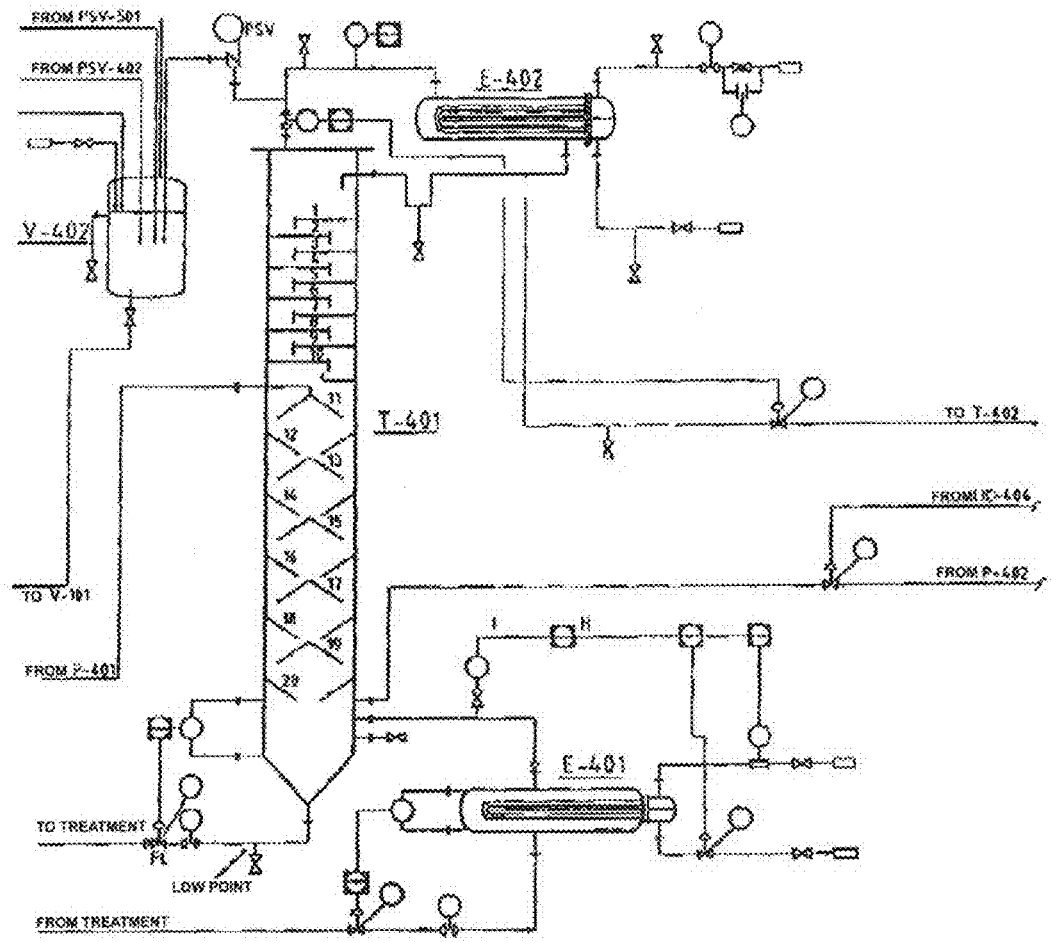
FIG. 6 shows the rectification section of the distillation unit (400).
Figure 7:
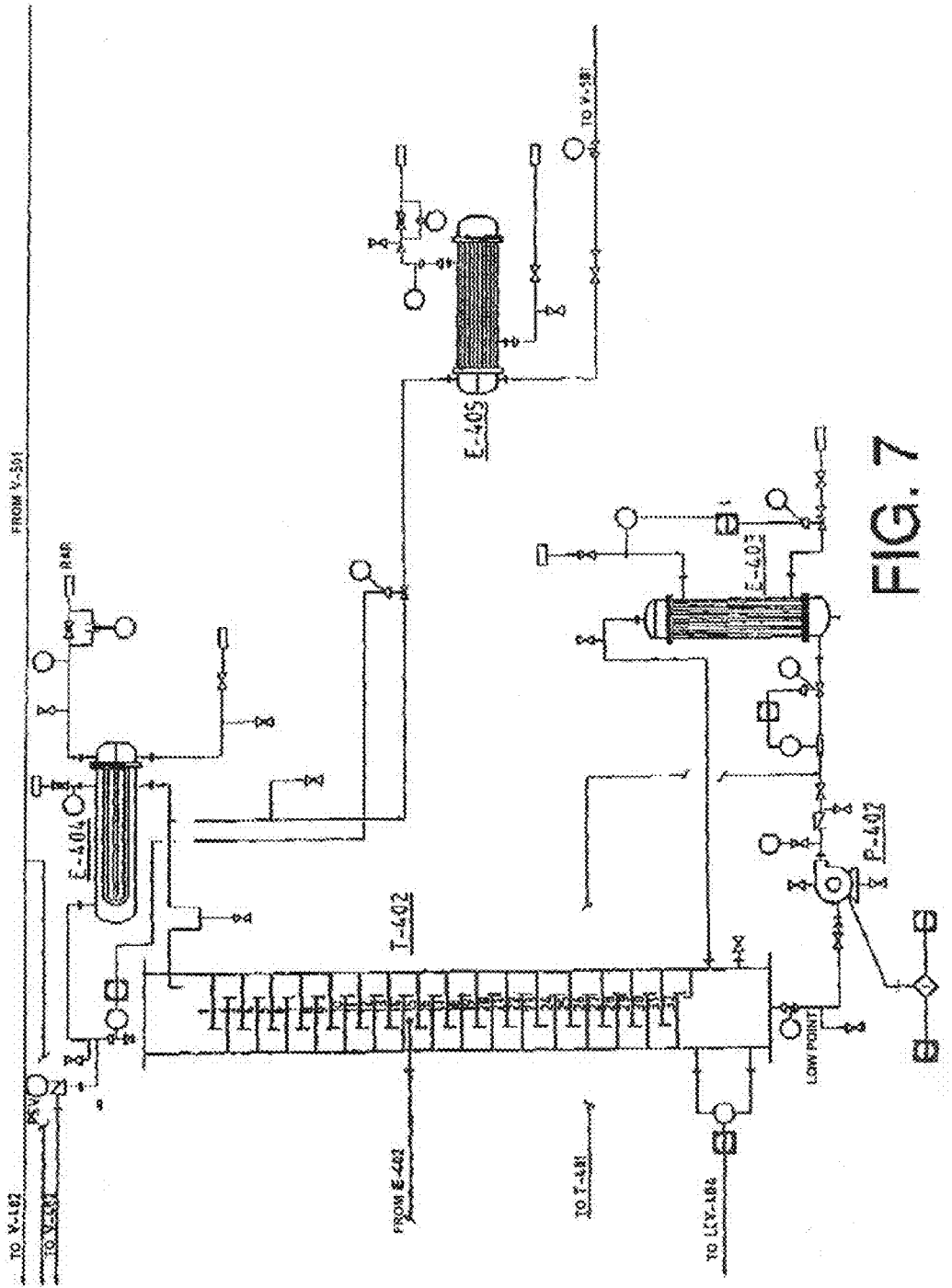
FIG. 7 shows the azeotropic distillation section of the distillation unit (400).
Figure 8:
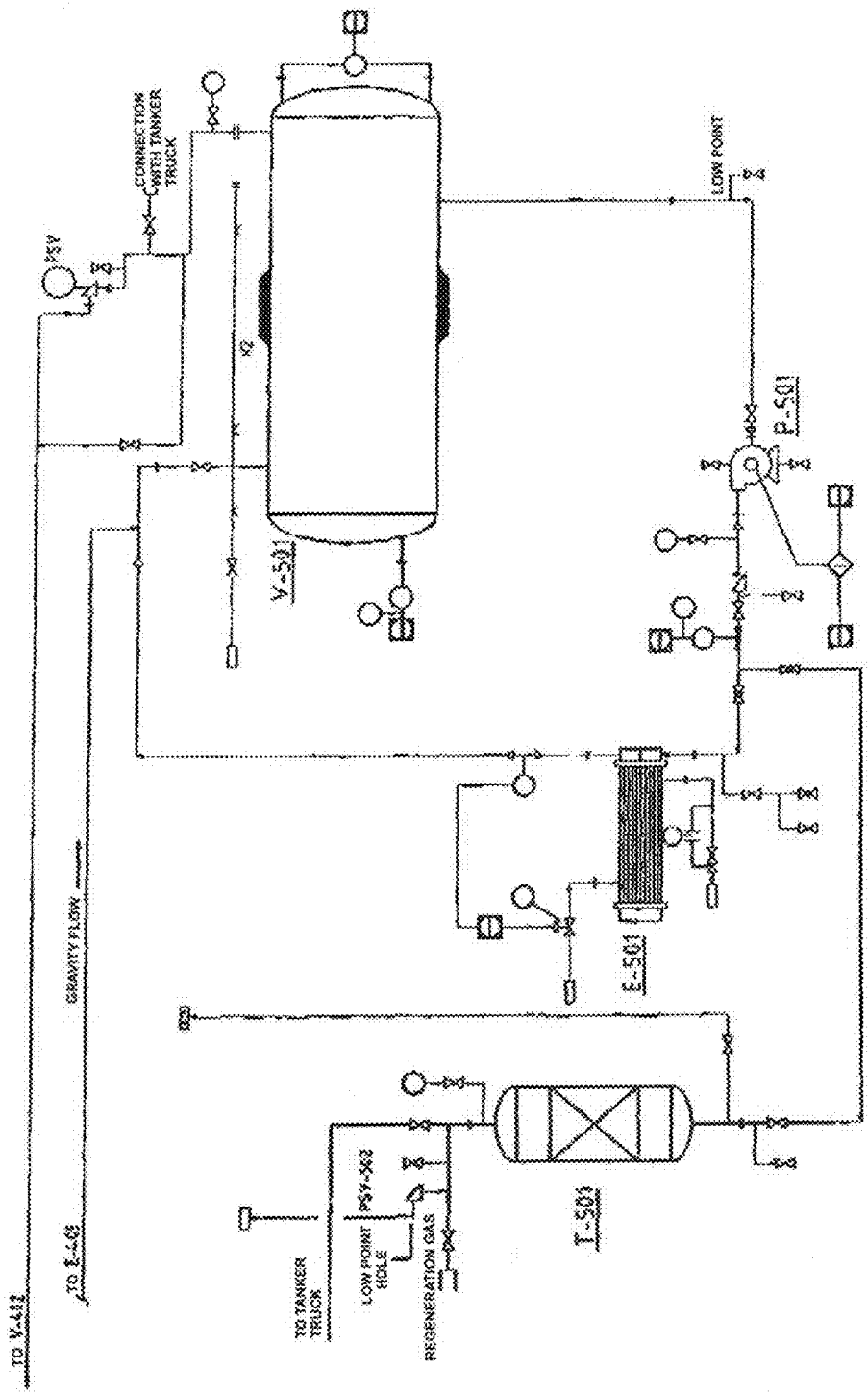
FIG. 8 shows the bioethanol dehydration unit (500).
Figure 9:
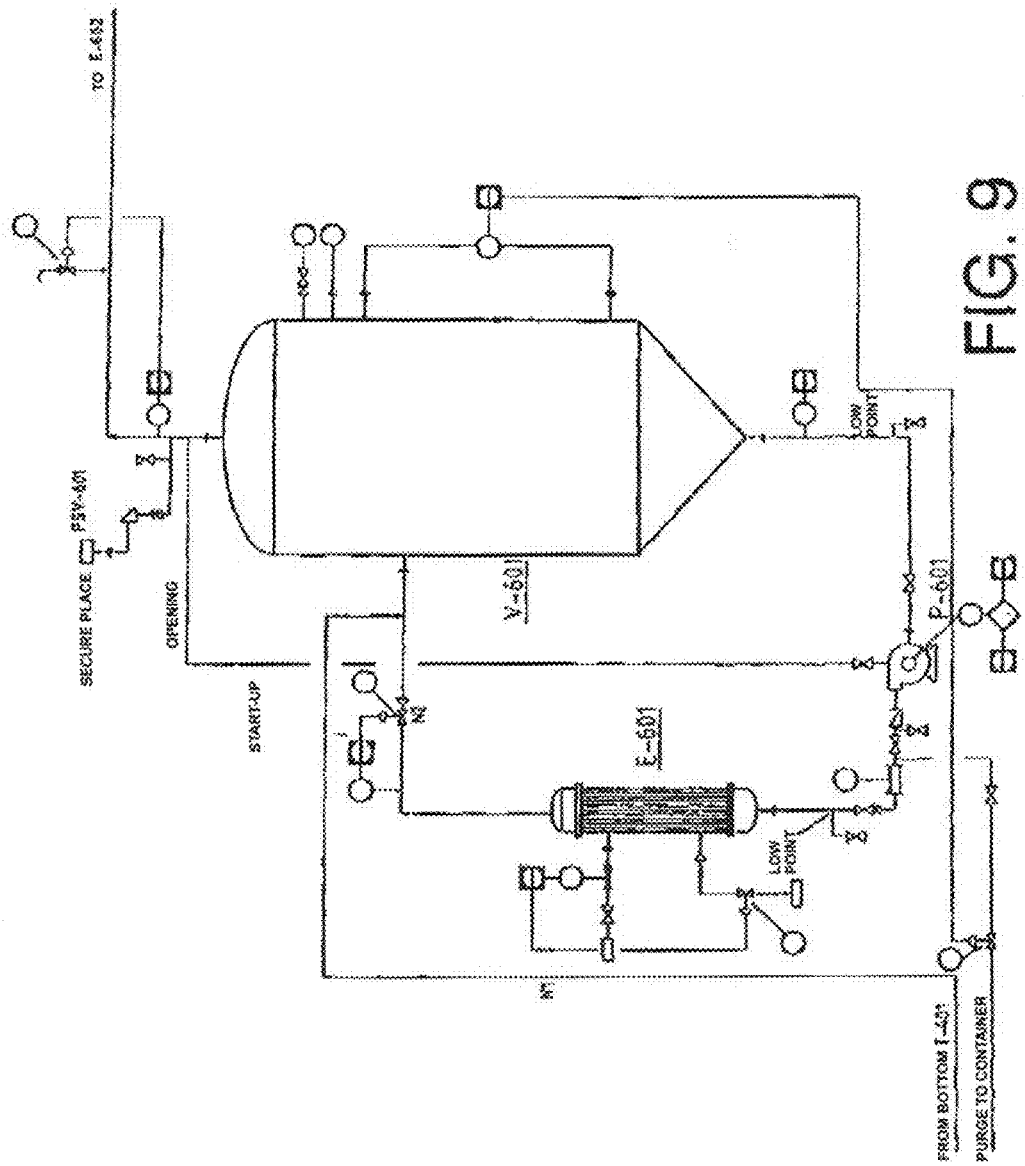
FIG. 9 shows the effluents treatment unit (600), specifically, the vacuum evaporation section.
Figure 10:
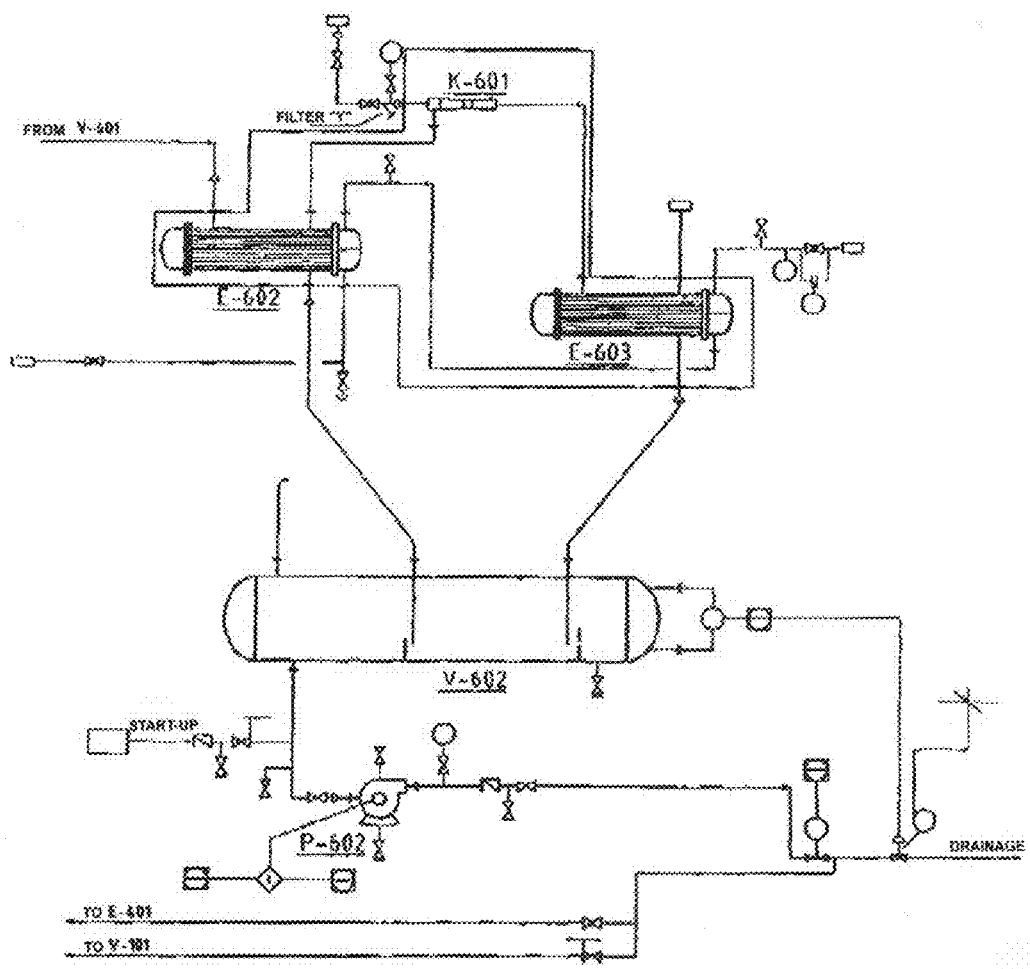
FIG. 10 shows the effluents treatment unit (600), specifically, the recovered water condensation section.
Figure 15:
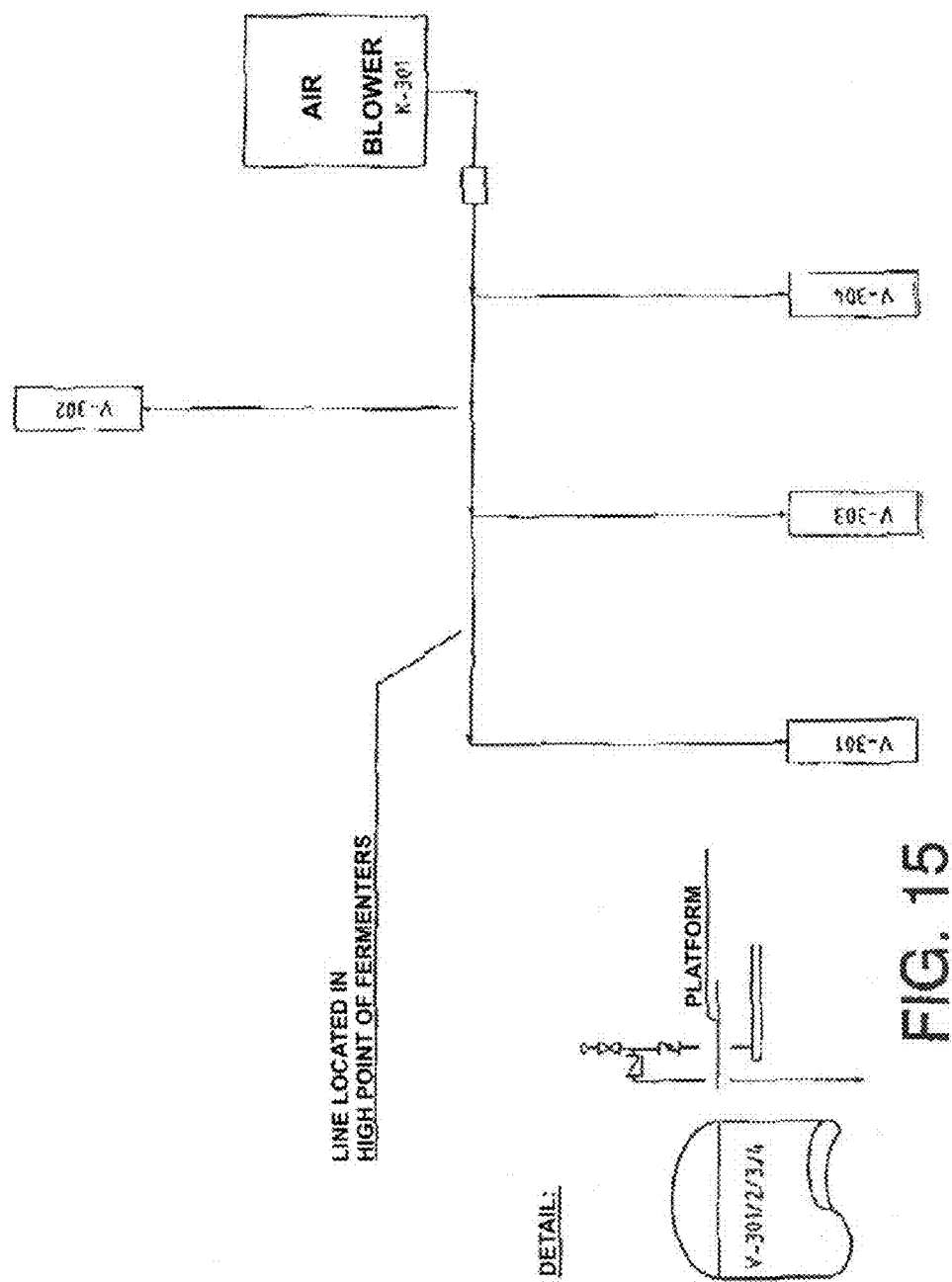
FIG. 15 shows a diagram of the distribution of air to the fermenters.

In FIG. 1:
V-101 Vessel for the preparation of the reactors charge
P-101 Feed pump to reactors
V-102 Vessel for the reactor product
P-102 Feed pump to fermenters
E Input of organic waste
A-102 Analyzer
In FIG. 2A:
R-101 A/B Prehydrolysis reactors
XV112B, XV-106A, XV115A and XV104A: Valves
N1 Locate at least 2 m above V-102
N2 Locate the TCV-101A at a minimum distance from R101A N3 Locate valves XV-112A and B at a minimum distance from R101A and E-101B, respectively
N4 Connection for reducer flange sample collector.
In FIG. 2B:
TT101 Temperature transmitter
R-101B Prehydrolysis reactor
A-103B Analyzer
N1 Locate at least 2 m above V-102
N2 Locate TCV-101B at a minimum distance from R101B
N3 Locate peak as close as possible to V402
N4 Connection for reducer flange sample collector.
In FIG. 3:
P-103 Cooling pump for the reactors R-101 A/B
E-101 Prehydrolysis cooler.
In FIG. 4:
V-301/304 Fermenter vessels
P-301/304 Fermentation product pumps
E-301/304 Coolant for the fermentation broth
XV-320, XV321: Valves
N1 Accessible from upper platform (FIG. 15)
In FIG. 5:
V-401 Feed vessel
P-401 Feed pump
A-401 Analyzer.
In FIG. 6:
T-401 Rectifying column
E-402 Column condenser
E-401 Column boiler
V-402 Safety valve vessel
LIC Level controller
In the lower left-hand part of this figure, the upper point where it states "to treatment" continues with FIG. 9 and the lower point with the legend "to treatment" continues with FIG. 10.
In FIG. 7:
T-402 Azeotropic column
E-404 Column condenser
E-403 Column boiler
E-405 Bioethanol cooler
P-402 Bottom pump
LCV: Level control valve
V-501 Wet bioethanol tank.
In FIG. 8:
V-501 Wet bioethanol tank
P-501 Wet bioethanol pump
E-501 Bioethanol cooler
T-501 Drying tower
N2 Fireproof insulation
In FIG. 9:
V-601 Vacuum separator
P-601 Concentrates pump
E-601 Evaporator
N1 Line with flow in two phases, support to prevent vibrations,
Locate valve PCV-605 close to the input for V-601.
In FIG. 10:
V-602 Recovered water accumulator
P-602 Pump for water to treatment
K-601 Ejector
E-602 Pre-condenser
E-603 Post-condenser.

Figure 11:
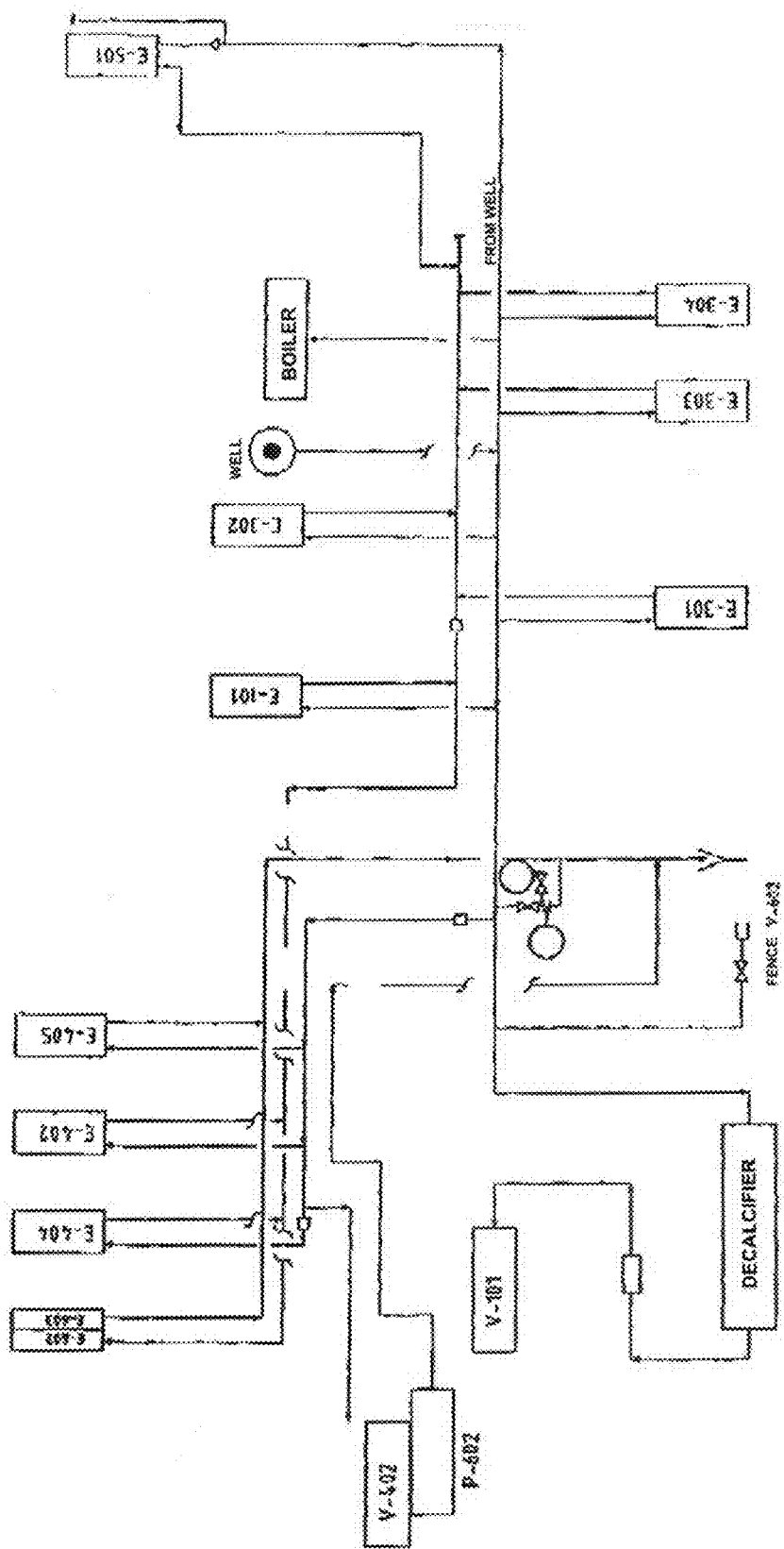
FIG. 11 shows the cooling water supply and return section.
Figure 12:
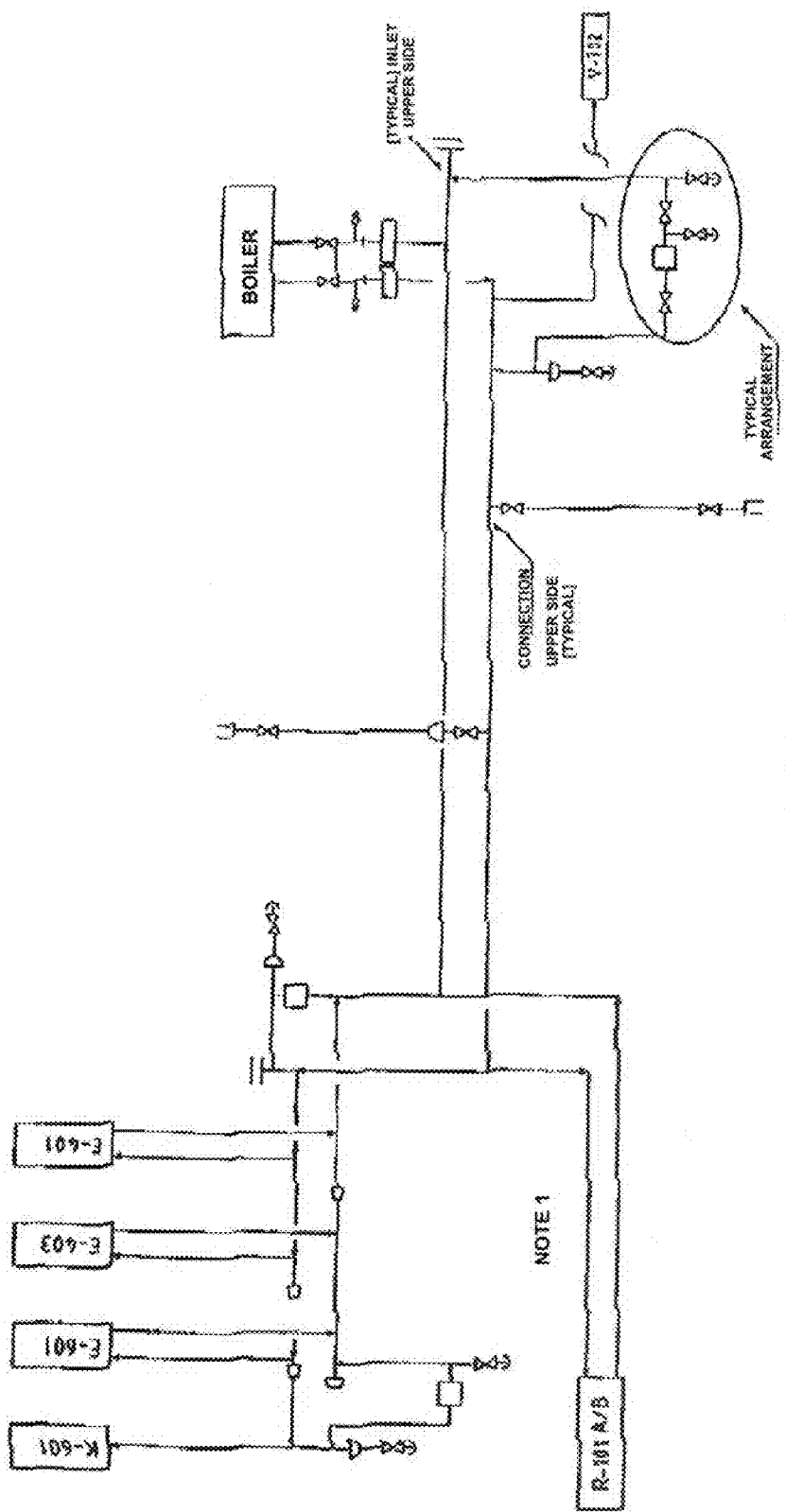
FIG. 12 shows a flow diagram of the steam and condensate.
Figure 13:
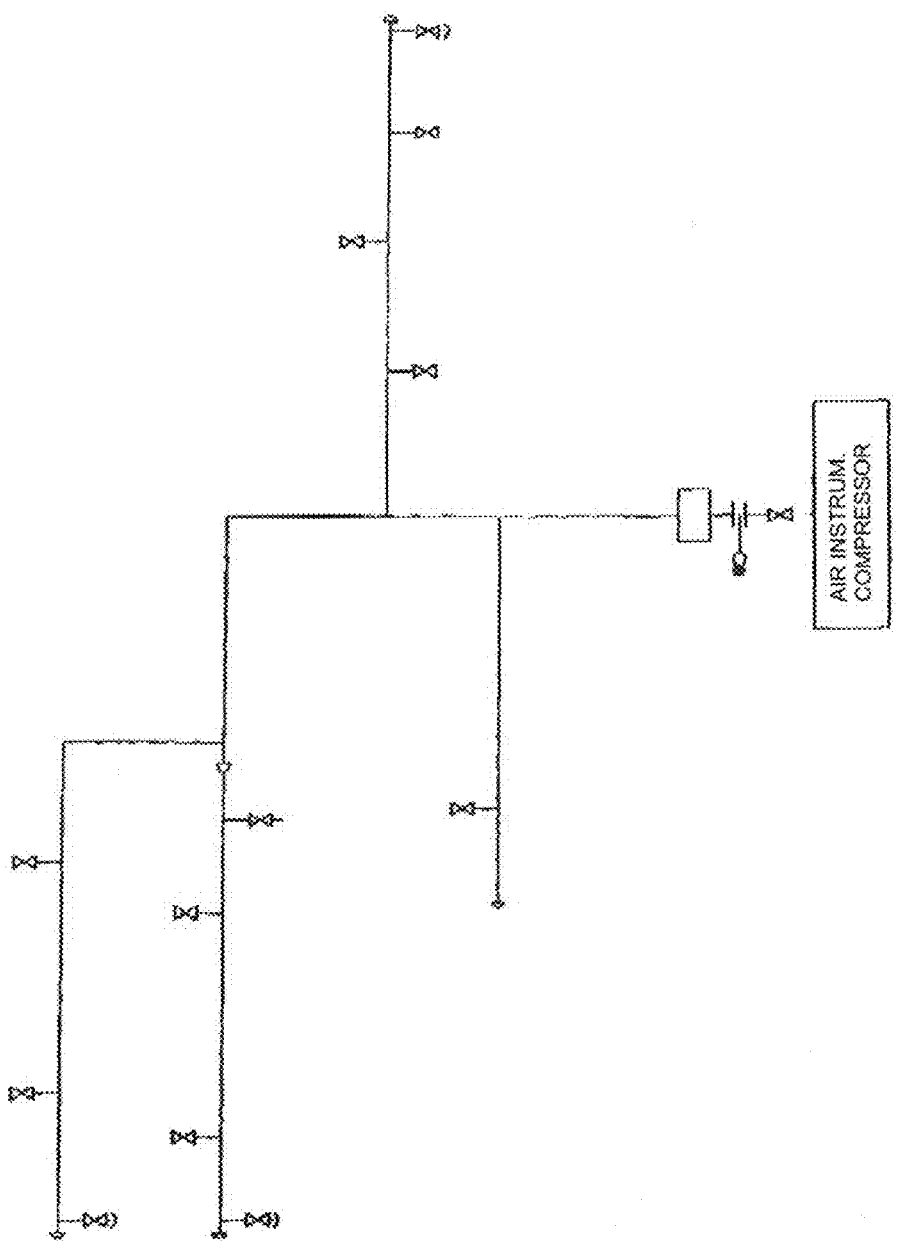
FIG. 13 shows a diagram of the air/instruments facility.
Figure 14:
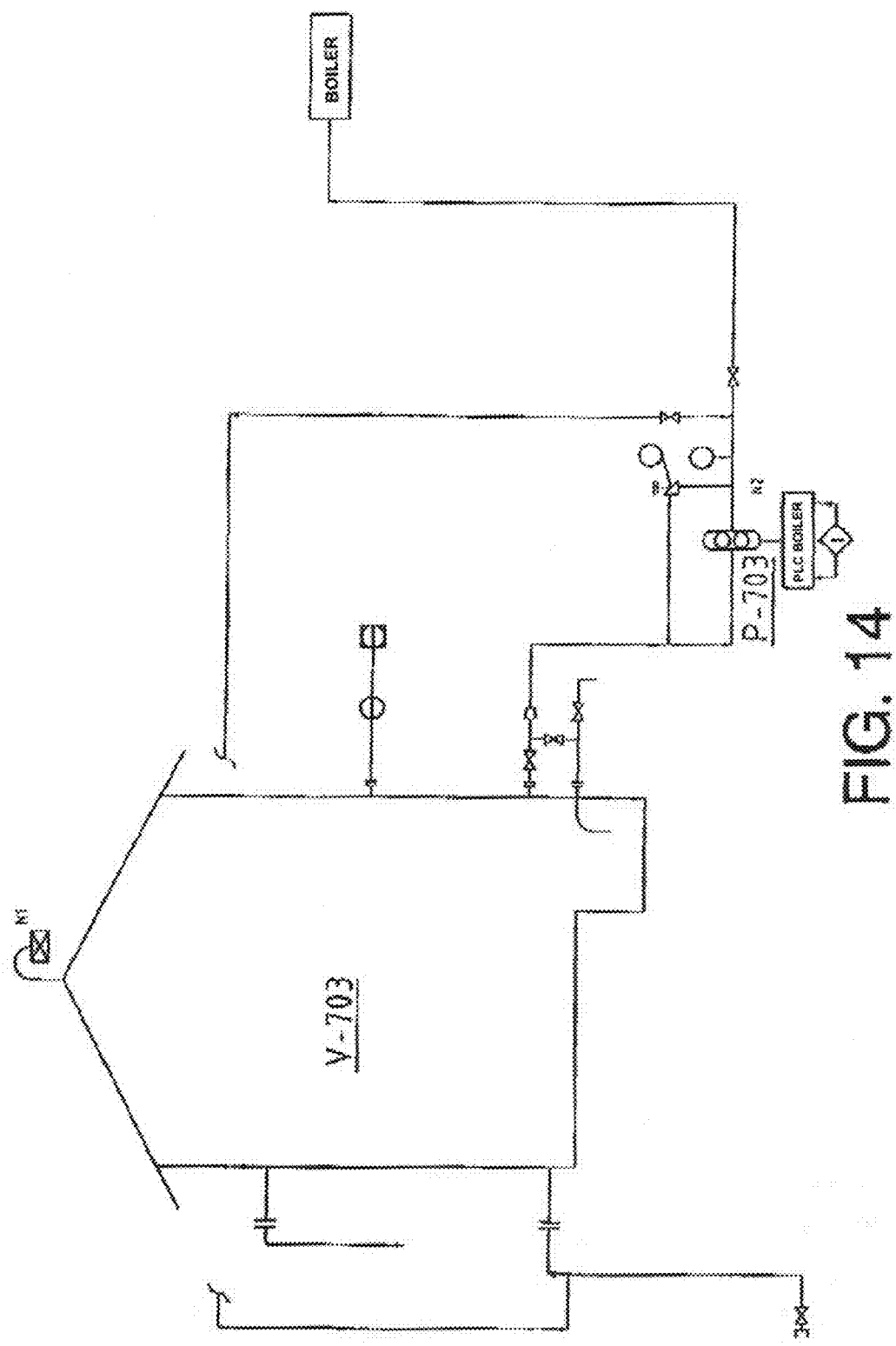
FIG. 14 shows a diagram of the gasoil distribution.
Figure 16:
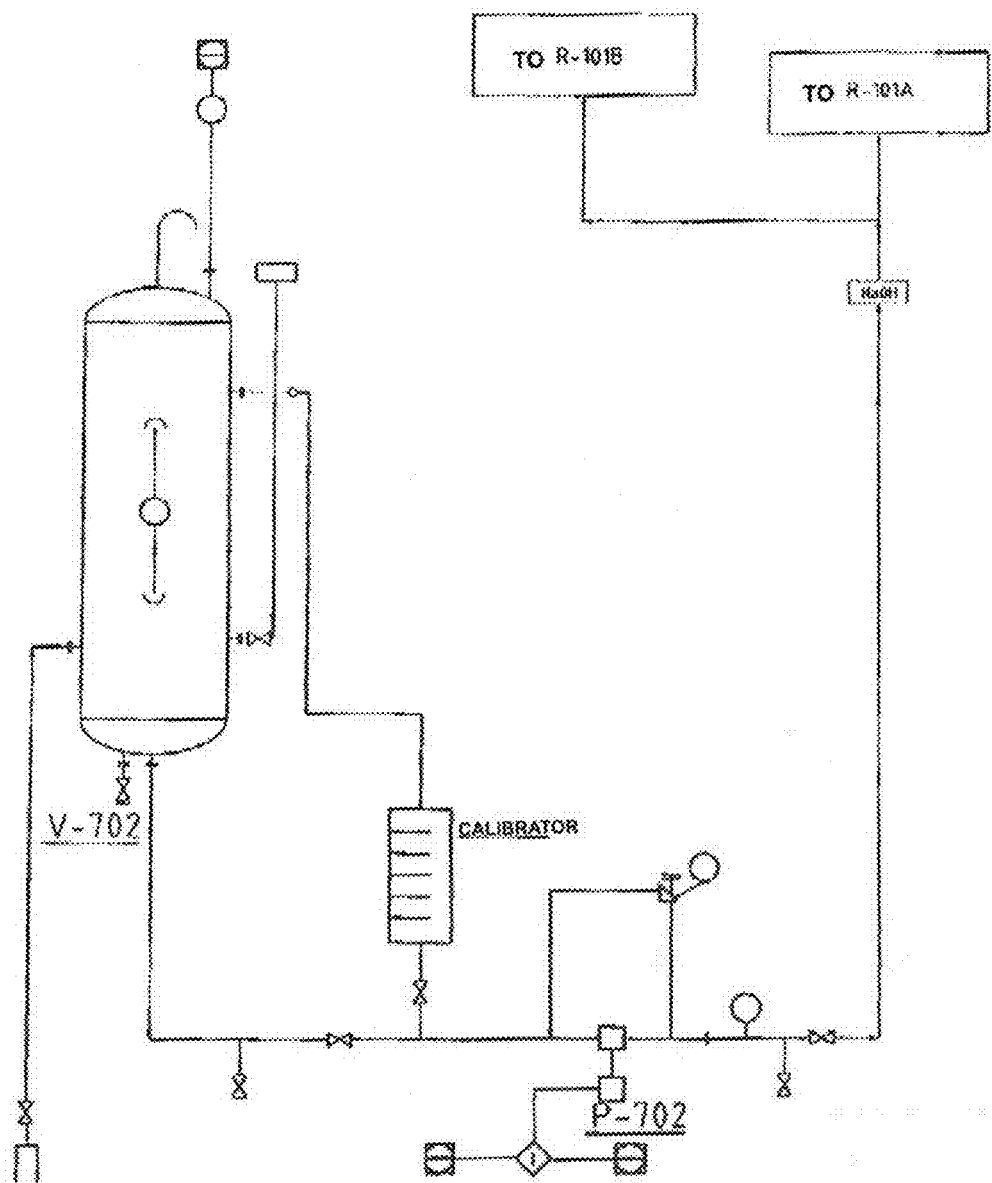
FIG. 16 shows a diagram of the distribution of soda (NaOH).
Figure 17:
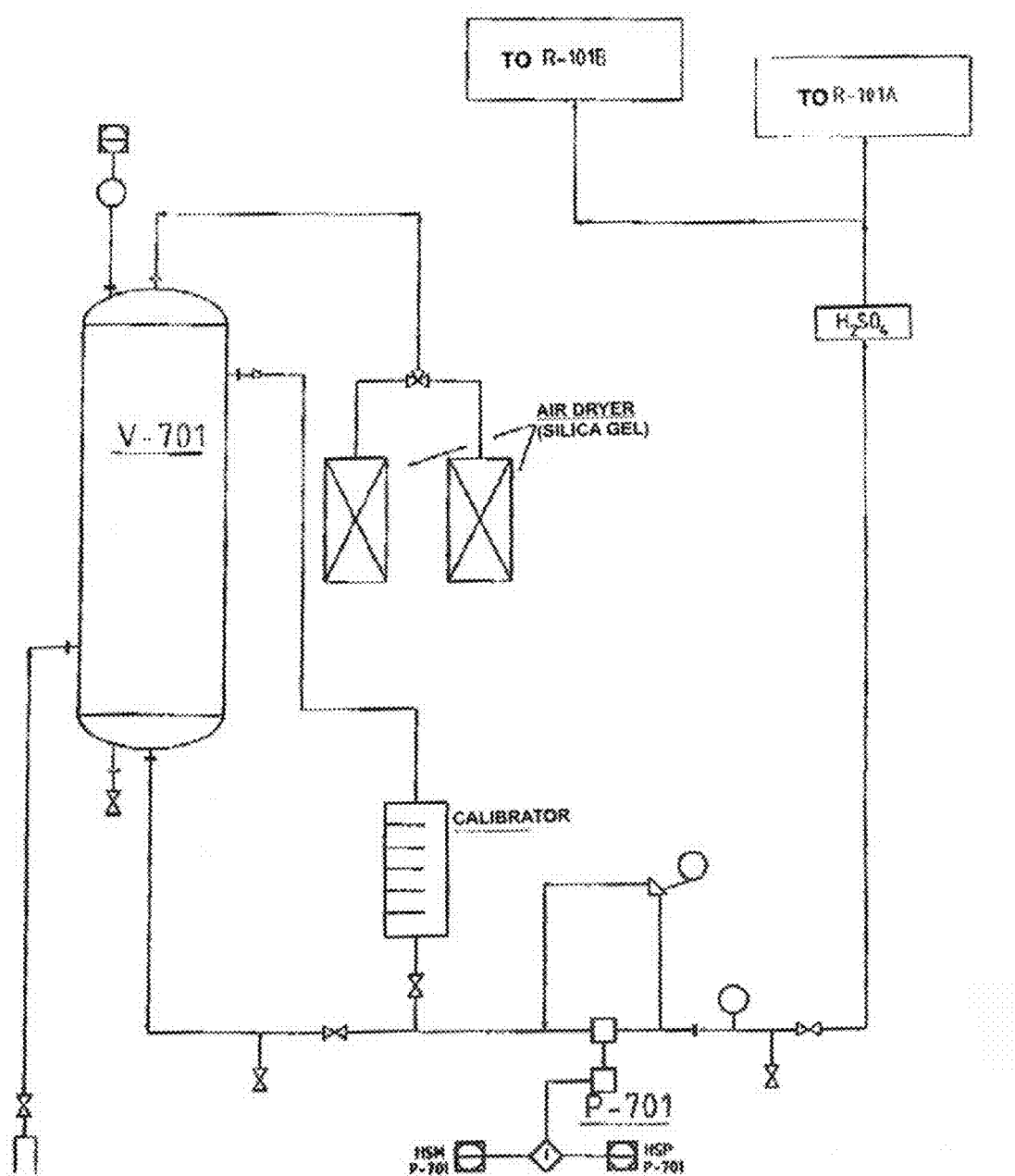
FIG. 17 shows a diagram of the distribution of sulfuric acid ($H_2SO_4$).

In FIGS. 11, 12 and 13, the references mean the same as stated in the other figures in which the same elements appear.
In FIG. 14:
V-703 Gasoil tank
P-703 Gasoil pump
In FIG. 16:
V-702 Soda accumulator
P-702 Soda pump
In FIG. 17:
V-701 Acid accumulator
P-701 Acid pump
In general in the figures:
TT Temperature transmitters
PSV Safety valves
PLC Control system
I Instrumentation
M Motors

The invention claimed is:

1. A method for recovering energy from the organic fraction of urban solid waste comprising the following steps:
    a) pretreatment of said organic fraction in a completely mixed type reactor, of conical design and with internal stirring by means of Archimedes screw with sulfuric acid at a concentration between 0.1 and 5% by volume, at a temperature between 120° C. and 140° C. and for a time of between 30 and 90 minutes by heating by an outer thermal jacket with no steam injection or steam explosion, producing a first slurry containing an insoluble solid susceptible to enzymatic attack by cellulases;
    b) a step comprising enzymatic hydrolysis by cellulases and simultaneous fermentation, using an ethanol yeast producer of said first slurry at a temperature between 35° C. and 42° C., employing cellulases at an amount of between 10 and 40 FPU/gram during a time of less than 140 hours in order to obtain a second slurry containing diluted ethanol;
    c) distillation of said second slurry to obtain wet ethanol, a recyclable liquid effluent and a solid.

2. A method according to claim 1, wherein the pretreatment stage with acid is carried out at a concentration preferably between 0.5% and 1% by volume.

3. A method according to claim 1, wherein said method is carried out with a charge of initial solids of between 5-40% weight/volume, preferably between 10-30% weight/volume.

4. A method according to claim 1, wherein the pretreatment stage with acid is carried out with a residence time preferably between 40 and 60 minutes.

5. A method according to claim 1, wherein the distillation is carried out in two stages: rectification by steam stripping, and azeotropic distillation.

6. A method according to claim 1, wherein distillation of the second slurry obtained following the enzymatic hydrolysis by cellulases and simultaneous fermentation is carried out by means of a stripping process in a rectification column of the distillation process.

7. A method according to claim 6, wherein the rectification column consists of a screen plates rectification column.

8. A method according to claim 1, further comprising a dehydration stage of the ethanol.

9. A method according to claim 1, further comprising a stage of treatment and recovery of effluents.

* * * * *